US011707510B2

(12) United States Patent
Füner

(10) Patent No.: US 11,707,510 B2
(45) Date of Patent: Jul. 25, 2023

(54) NUCLEIC ACID-BASED BOTULINUM NEUROTOXIN FOR THERAPEUTIC USE

(71) Applicant: preclinics discovery GmbH, Potsdam (DE)

(72) Inventor: Jonas Füner, Potsdam (DE)

(73) Assignee: PRECLINICS DISCOVERY GMBH, Potsdam (DE)

( * ) Notice: Subject to any disclaimer, the term of this patent is extended or adjusted under 35 U.S.C. 154(b) by 0 days.

(21) Appl. No.: 16/970,320

(22) PCT Filed: Feb. 18, 2019

(86) PCT No.: PCT/EP2019/053937
§ 371 (c)(1),
(2) Date: Aug. 14, 2020

(87) PCT Pub. No.: WO2019/158745
PCT Pub. Date: Aug. 22, 2019

(65) Prior Publication Data

US 2021/0077597 A1 Mar. 18, 2021

(30) Foreign Application Priority Data

Feb. 16, 2018 (DE) .................... 10 2018 103 504.7

(51) Int. Cl.
*A61K 38/48* (2006.01)

(52) U.S. Cl.
CPC .. *A61K 38/4893* (2013.01); *C12Y 304/24069* (2013.01)

(58) Field of Classification Search
CPC ................................................. A61K 38/4893
See application file for complete search history.

(56) References Cited

U.S. PATENT DOCUMENTS 6,760,788 B2 * 7/2004 Knight .................. G06F 13/387
710/62
6,967,088 B1 * 11/2005 Williams ............. C07K 14/245
435/71.1
7,556,817 B2 * 7/2009 Steward .................. A61P 17/00
435/471
7,670,780 B2 * 3/2010 Hogan ................. C12Q 1/6895
435/6.15
7,815,917 B2 * 10/2010 Steward .................. A61P 35/00
435/471
7,825,233 B2 * 11/2010 Steward ................. C07K 14/33
536/23.7
8,586,329 B2 * 11/2013 Hofmann .................. A61P 9/14
536/23.7
9,186,396 B2 * 11/2015 Frevert .................... C12N 9/96
9,216,210 B2 * 12/2015 Dolly ...................... C07K 14/33
9,511,114 B2 * 12/2016 Hofmann ........... A61K 38/4893
9,809,809 B2 * 11/2017 Schmidt ............. C07K 14/4746
9,827,298 B2 * 11/2017 Hofmann ................ A61P 17/02
9,878,056 B2 * 1/2018 Bancel ................. C07K 14/535
10,030,238 B2 * 7/2018 Cossins .................... C12N 9/52
10,087,432 B2 * 10/2018 Rummel ................ A61P 21/02
10,190,110 B2 * 1/2019 Dong ...................... A61P 21/00
10,266,816 B2 * 4/2019 Rummel ................ A61P 25/06
10,307,468 B2 * 6/2019 Palan ...................... A61P 13/10
10,451,621 B2 * 10/2019 Wang .................. G01N 33/573
10,457,927 B2 * 10/2019 Dolly ................ A61K 38/4893
10,501,731 B2 * 12/2019 Steward ......... C12Y 304/24069
10,703,806 B2 * 7/2020 Fernandez-Salas ..... A61P 25/02
10,704,035 B2 * 7/2020 Collier ..................... C12N 9/52
10,709,772 B2 * 7/2020 Csikos ................ A61K 9/0053
10,725,025 B2 * 7/2020 Jatzke ...................... G02B 5/30
10,772,945 B2 * 9/2020 Fuener ................... C07K 16/18
10,772,975 B2 * 9/2020 Bancel ................. C07K 14/535
10,786,438 B2 * 9/2020 Krishnan ................. A61K 8/64
10,808,236 B2 * 10/2020 Rummel ................ C07K 14/33
10,844,362 B2 * 11/2020 Dong ...................... A61P 21/00
10,883,096 B2 * 1/2021 Rummel ................ A61P 27/02
11,034,947 B2 * 6/2021 Anderson .............. A61P 35/00
11,066,451 B2 * 7/2021 Hackett .......... C12Y 304/24069
11,104,891 B2 * 8/2021 Dong ...................... A61P 25/04
11,117,935 B2 * 9/2021 Dong ....................... C12N 9/52
11,149,262 B2 * 10/2021 Jacky ...................... A61P 13/10
11,193,931 B2 * 12/2021 Gray ...................... C07K 16/18
2002/0107199 A1 * 8/2002 Walker .............. A61K 38/4893
514/18.6
2007/0166332 A1 * 7/2007 Steward .................. A61P 27/16
435/471

(Continued)

FOREIGN PATENT DOCUMENTS

EP 2154151 A2 * 2/2010 ............ C07K 14/33
EP 2377881 A2 * 10/2011 ............ C07K 14/33

(Continued)

OTHER PUBLICATIONS

International Search Report, International Patent Application No. PCT/EP2019/053937, dated May 17, 2019.

*Primary Examiner* — Brian Gangle
*Assistant Examiner* — Lakia J Jackson-Tongue
(74) *Attorney, Agent, or Firm* — Knobbe, Martens, Olson & Bear, LLP

(57) ABSTRACT

The invention relates to a botulinum neurotoxin-encoding nucleic acid for therapeutic use. The invention further relates to the transfection of skeletal muscle cells and smooth muscle cells and the glands of the skin, and of other skin cells with botulinum neurotoxin (BoNT)-encoding nucleic acids (RNA or DNA) with or without the use of a secretory signal, for therapeutic and/or cosmetic purposes.

14 Claims, 4 Drawing Sheets

Specification includes a Sequence Listing.

(56) References Cited

U.S. PATENT DOCUMENTS

| | | | | | |
|---|---|---|---|---|---|
| 2010/0075396 | A1* | 3/2010 | Steward | A61P 25/00 | 435/212 |
| 2011/0294742 | A1* | 12/2011 | Steward | A61P 1/00 | 514/17.7 |
| 2012/0115205 | A1* | 5/2012 | Steward | A61P 17/00 | 435/220 |
| 2014/0308267 | A1* | 10/2014 | Schmidt | A61K 38/4893 | 530/387.9 |
| 2015/0166616 | A1* | 6/2015 | Bancel | A61K 38/45 | 536/23.5 |
| 2018/0078632 | A1* | 3/2018 | Fuener | A61K 39/08 | |
| 2020/0407702 | A1* | 12/2020 | Stenmark | A61K 8/64 | |
| 2021/0077597 | A1* | 3/2021 | Füner | A61K 31/7088 | |
| 2021/0115101 | A1* | 4/2021 | Bancel | C12N 9/2402 | |
| 2021/0277377 | A1* | 9/2021 | Jacky | A61P 17/02 | |

FOREIGN PATENT DOCUMENTS

| | | | | |
|---|---|---|---|---|
| EP | 3333179 | A1 * | 6/2018 | |
| EP | 3728295 | A1 * | 10/2020 | A61K 38/4893 |
| EP | 3728296 | A1 * | 10/2020 | A61K 38/4893 |
| EP | 3752128 | A1 * | 12/2020 | A61K 31/7088 |
| WO | WO 2004/071538 | A2 | 8/2004 | |
| WO | WO-2005035730 | A2 * | 4/2005 | C07K 14/33 |
| WO | WO-2006011966 | A1 * | 2/2006 | C07K 14/33 |
| WO | WO-2006017749 | A2 * | 2/2006 | C07K 14/33 |
| WO | WO 2006/076902 | A2 | 7/2006 | |
| WO | WO-2013068476 | A1 * | 5/2013 | A61K 38/4893 |
| WO | WO 2013/091895 | A1 * | 7/2013 | |
| WO | WO 2014/152121 | A1 | 9/2014 | |
| WO | WO-2014152121 | A1 * | 9/2014 | A61K 39/08 |
| WO | WO 2016/131052 | A1 | 8/2016 | |
| WO | WO-2016162553 | A1 * | 10/2016 | A61K 39/08 |
| WO | WO 2017/220800 | A1 | 12/2017 | |
| WO | WO-2018158745 | A1 * | 9/2018 | B29C 35/0805 |
| WO | WO-2021186160 | A2 * | 9/2021 | A61K 38/4893 |
| WO | WO-2021186167 | A1 * | 9/2021 | |

* cited by examiner

Antigen retrieval Tris/EDTA pH8,9
Anti-Fluc Ab, d200, 1h

Digit Abduction Score after treatment with BoNT-A-encoding RNA 1.6
1.4
1.2
1
0.8
0.6
0.4
0.2
0

DAS score 0 10 20 30 40 50 60 70 80

Hours after (last) application

Vector only without RNA
Vector with BoNT-RNA
Antitoxin + vector with BoNT-RNA
twice application of vector with BoNT-RNA Examples from the Digit Abduction Score for the assessment of paralysis

- Treatment with transfection vector only

- Treatment with transfection vector and BoNT-RNA

NUCLEIC ACID-BASED BOTULINUM NEUROTOXIN FOR THERAPEUTIC USE

FIELD OF THE INVENTION

The invention relates to a botulinum neurotoxin-encoding nucleic acid for therapeutic use. The invention further relates to the transfection of skeletal muscle cells and smooth muscle cells and the glands of the skin, and of other skin cells with botulinum neurotoxin (BoNT)-encoding nucleic acids (RNA or DNA) with or without the use of a secretory signal, for therapeutic and/or cosmetic purposes.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 56311014 1.TXT, the date of creation of the ASCII text file is Sep. 16, 2022, and the size of the ASCII text file is 49.4 KB.

BACKGROUND

Botulinum neurotoxins (BoNT) are produced by the spore-forming bacteria *Clostridium botulinum* in at least 7 serotypes and at least 30 subtypes. The expression occurs from a characteristic gene cluster together with a number of complex proteins, several hemagglutinins and a non-toxin-non hemagglutinin molecule of similar size as the neurotoxin itself. Neurotoxin serotype A (as an example) has a molecular weight of 150 kDa and consists of 2 domains, the heavy chain (100 kDa) and the light chain (50 kDa), which are still connected by a disulfide bond after activation. The heavy chain domain in turn consists of the translocation domain at the N-terminus by means of which the light chain is transported from the vesicle into the cytosol. At the C-terminal, the heavy chain domain contains the binding domain that binds to presynaptic gangliosides and to the vesicular SV2 protein. The light chain develops catalytic activity after translocation into the cytosol and specifically cuts the SNARE protein SNAP-25 after glutamine$^{197}$. As a result, the SNARE complex loses density and can no longer pull the vesicle with the neurotransmitter sufficiently firmly to the inner side of the membrane of the presynaptic terminal, so that there is no longer a fusion with the cell membrane and corresponding release of the stored neurotransmitter into the synaptic cleft. The physiological consequence of this chemical denervation is post-synaptic muscle paralysis. The mechanism of action of botulinum neurotoxins comprises 4 steps:

1. the binding of the heavy chain and Gt1b and SV2 at the presynaptic terminal or at the exposed release vesicle,
2. the uptake into the release vesicle when it is retracted into the presynaptic terminal,
3. the translocation of the light chain from the vesicle into the presynaptic cytosol, and
4. the catalytic processing of SNAP-25 by the light chain in the cytosol.

The complex proteins expressed from the same gene cluster form different complexes with the neurotoxin, which protect the neurotoxin against the low pH values in the stomach and proteolytic enzymes until the complex dissociates in the duodenum at alkaline pH values and the neurotoxin probably again paracellularly with the help of the hemagglutins through the mucosa is absorbed into the blood. This mechanism only plays a role in the naturally occurring function of the neurotoxin as a feeding poison, while it is injected intramuscularly or intraglandularly in therapeutic uses in medicine, the toxin action also working without the complex proteins.

Botulinum neurotoxin has long been approved as a drug (e.g. BOTOX, Xeomin, Dysport, Myobloc).

The botulinum neurotoxin (BoNT) is particularly known for its use in aesthetic medicine, less well-known is the extraordinary importance for the treatment of spasticity and dystonia, as well as the reduction of hyperhidrosis or saliva leakage, which is usually due to reduced swallowing ability (e.g. in Parkinson's disease, amyotrophic lateral sclerosis, infantile cerebral palsy).

The effect is based on the inhibition of the transmission of excitation on the presynaptic part of the motor end plate and the associated paralysis of the muscle cell or, in the case of the salivary glands, the autonomous innervation of the gland cells.

On the other hand, BoNT is one of the strongest toxins and a dose of less than 1 mg can already lead to the death of a person.

The duration of the effect varies depending on the dose used and the BoNT serotype used. Usually BoNT/A is used, but there are also BoNT/B preparations, e.g. Neurobloc with a shorter duration of action. BoNT/E Products are not yet on the market, but there are already advanced developments for such a product.

In the case of chronic diseases, a particularly long duration of action is sought, since the treatment procedure is uncomfortable for the patient and is associated with pain. In addition, the treatment costs are quite high, since the treatment can only be carried out by doctors with special experience. Furthermore, the dose and the number of treatments increase the risk that the patient will develop neutralizing antibodies against BoNT and thereby become a secondary non-responder for whom this valuable and often only therapy is then no longer available.

To get a long duration of action, it is necessary to administer a rather high dose. However, with the previous therapeutic method, the application of BoNT in solution, the systemic dose is also increased with an increase in the local dose. Increasing the systemic dose can lead to serious side effects and is therefore risky. As a rule, the duration of action of injected BoNT/A protein is limited to approximately 3-4 months.

BoNT drugs are either produced in clostridia or recombinantly in a suitable expression system such as *E. coli*. Appropriate safety zones are required for both and large amounts of toxin have to be handled. This is also a social risk, since there is always a risk of theft and misuse if there are large amounts of toxins. After all, BoNT belongs to category A of biological warfare agents according to the classification of the Center for Disease Control (USA). A further complication is that even the highly regulated, pharmaceutical-industrial production is subject to biological fluctuations and that for each batch an activity control must therefore be carried out or the preparations must be biologically standardized. One "unit" corresponds to the amount of botulinum toxin which, after intraperitoneal administration, is fatal in mice and leads to the death of 50% of the treated animals (LD50). Here, a test is used that has largely been abolished in other areas of toxicology. Although cell-based alternative methods have recently been developed, many animal experiments are still being carried out for these tests.

One disadvantage is that the therapeutic index of BoNT is very small; this is of course less important in aesthetic applications such as frown lines on the forehead than in high-dose applications such as spasticity after a stroke or infantile cerebral palsy. Due to the high toxicity, there is always the risk of overdosage with side effects that are systemic or distant from the injection site. The duration of the effect is long but nevertheless limited. Since the medicament is injected locally intramuscularly or intraglandularly, the treatment is also uncomfortable and associated with pain.

Due to the numerous and various disadvantages, it would therefore be good if the production of the toxin could be dispensed with and there would be a standardized drug that would not pose a risk to people or the environment. It would also be advantageous to avoid the risk of overdosing or to greatly reduce systemic side effects. It would also be very advantageous to get more options when setting the duration and potency.

The object of the invention was therefore to provide an alternative medicament for the previous BoNT active ingredient which overcomes the disadvantages of the prior art.

SUMMARY

The object is attained by the features of the independent claims. Preferred embodiments are specified in the dependent claims.

In a first preferred embodiment, the invention relates to a nucleic acid for use as a drug and/or in therapeutic methods which comprise or consist of a botulinum neurotoxin-encoding nucleic acid.

The invention thus also relates to the use of BoNT nucleic acid for the transfection of cells so that these cells produce the BoNT protein themselves and transport it to the site of action.

The dosage of the expression of a recombinant product cannot be dosed as precisely as the direct injection of a dissolved protein. This is probably one of the reasons why the prior art has not yet described the recombinant therapy variant using nucleic acids applied to the muscle or skin. The fact that the dosage accuracy is less important in the gene therapy process because the systemic availability is significantly reduced is an important finding and thus a central component of the invention.

The invention thus also relates to the first use in gene therapy of a BoNT-encoding nucleic acid.

An advantage of the invention is that a longer duration of action can be achieved by applying the nucleic acid. Since the treatment procedure from the prior art (administration of the toxin itself) is uncomfortable for the patient and associated with pain, the treatment can be made significantly more pleasant.

The treatment costs can also be reduced in perspective with this new approach.

The nucleic acid according to the invention can then be transfected into the cells, for example muscle cells. The recombinant BoNT protein is then formed directly in the muscle cell and from there it reaches the site of action, the synaptic cleft.

According to the invention, the nucleic acids or nucleic acid molecules can also be present in a vector.

Muscle cells are particularly easy to transfect. After intramuscular or intradermal application of naked plasmid DNA or RNA with a corresponding transfection vector, expression of the recombinant protein in the target organ can be achieved relatively easily (see, for example, Davis, Whalen & Demeneix "Direct gene transfer into skeletal muscle in vivo: factors affecting efficiency of transfer and stability of expression" Hum Gene Ther. 1993 April; 4(2): 151-9; or Danko & Wolff, "Direct gene transfer into muscle." Vaccine. 1994 December; 12(16):1499-502).

In a preferred embodiment, the nucleic acid of the invention is prepared for direct application into the organ to be treated and/or muscle.

In a particularly preferred embodiment, the nucleic acid is prepared as DNA or RNA. The use of RNA is particularly preferred since the best results have so far been achieved with RNA.

The nucleic acid of the invention can also contain a promoter. However, experiments were also carried out with mRNA that did not require a promoter. In experiments with plasmid DNA, a CMV promoter was used that works well. However, other promoters can also be used, so that the invention should not be limited in this respect.

With BoNT therapy based on nucleic acids, the production of BoNT in the laboratory as a pharmaceutical can be dispensed with. Only the nucleic acids are made. The protein itself is produced in the body, for example in the patient's muscle cells.

By treating with nucleic acids and thus administering a recombinant BoNT in the cells at the target site, not only can a higher local dose be achieved, but this can also maintain the dose over a longer period of time.

In a further preferred embodiment, the invention relates to a nucleic acid comprising a BoNT-encoding nucleic acid and a S/MAR element. S/MAR stands for scaffold/matrix attachment region. These DNA sequences naturally occurring in all organisms anchor the DNA/chromatin to the nuclear matrix. Furthermore, these elements influence the expression of genes by interacting with or recruiting enhancers or not and by destabilizing the double helix structure.

It could be shown that S/MAR elements can prolong the expression of transfected DNA and the transfection of several cells is more homogeneous overall. It is believed that the also transfected S/MAR element ensures that the transfected DNA is not integrated into the host genome, but binds itself to the nuclear matrix. Thus, the DNA is not lost during cell division, but is also not integrated at an unfavorable point in the host genome. The latter usually leads to the silencing of the expression of the transfected gene or to side effects on the surrounding host genes. By means of the S/MAR element the negative aspects can be avoided.

Through various nucleic acid formulations (mRNA or plasmid DNA, different promoters, S/MAR etc.) a short or particularly long duration of action can be set. The person skilled in the art is able to identify the suitable formulation for the particular application without being inventive.

By releasing the protein directly at the site of action, the risk of overdosing is greatly reduced and the immunogenic potential is lowered.

In a particularly preferred embodiment, the invention relates to botulinum neurotoxin-encoding nucleic acids for the treatment of spasticity, dystonia and saliva leakage and/or hyperhydrosis.

The nucleic acid of the invention can therefore also be used in Parkinson's disease, amyotrophic lateral sclerosis or infantile cerebral palsy, since these clinical pictures can go hand in hand with reduced swallowing ability and can therefore lead, for example, to saliva leakage.

However, the nucleic acids of the invention can also be used in other diseases which are associated with movement disorders or impaired muscle activity.

DETAILED DESCRIPTION

Figure 1:
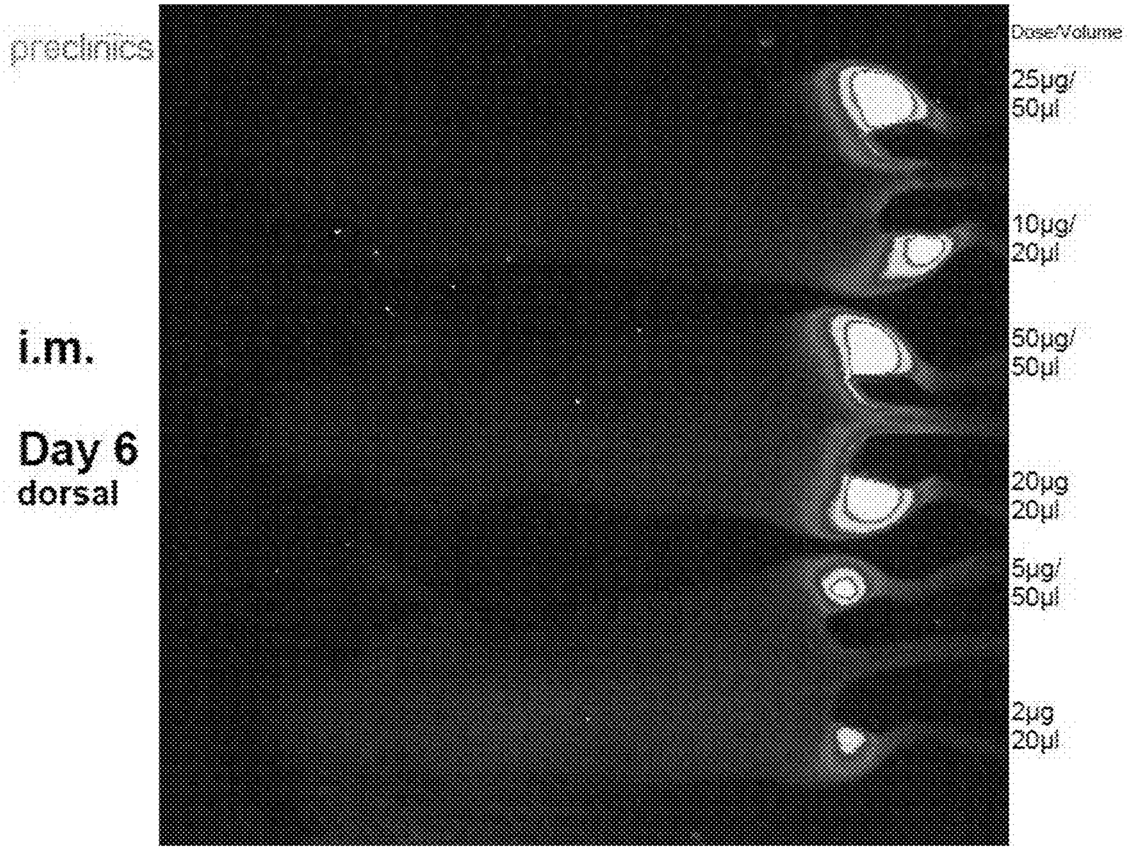
FIG. 1 shows a bioluminescence image which shows the luciferase expression 6 days after application of plasmid DNA (pEPI-1-luc) in different dosages, concentrations and volumes.
Figure 2:
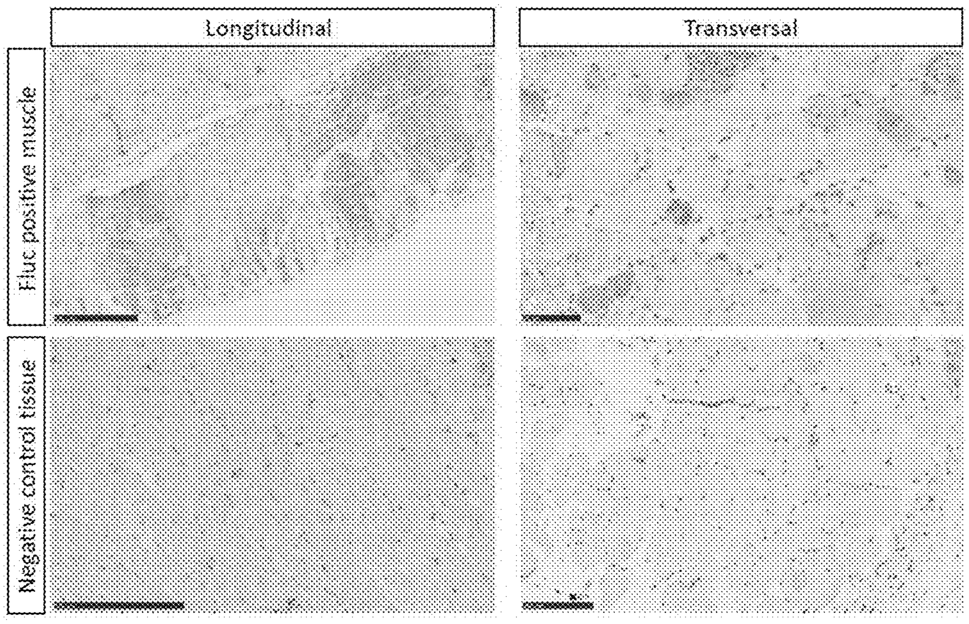
FIG. 2 shows an immunohistological staining of expressed luciferase in tissue after an injection of plasmid DNA into the muscle (gastrocnemius muscle) of the mouse. It can be clearly seen that the expression is restricted to the muscle cells and that no luciferase can be seen in the extracellular space.

It was completely surprising that the invention can be successfully implemented with and without a secretory signal can be successfully implemented. The transfection of the skeletal muscle cell without a secretory signal leads to an intracellular expression of the BoNT. Contrary to expectations, the BoNT from the cytoplasm reaches the synaptic cleft of the motor end plate and thus to the site of action, the presynaptic cholinergic nerve terminal. In this way a toxic systemic effect is avoided. The disadvantage of this method is that only the nerve terminals in the vicinity of the transfected cells are paralyzed and thus the uniform distribution of the transfection is a prerequisite for success. This disadvantage can be avoided by using a secretory signal, but it is nevertheless noteworthy that BoNT reaches the site of action even without this signal. Depending on the indication, this embodiment can be advantageous. When the secretory signal is used, the BoNT also reaches the extracellular space outside the neuromuscular synapse, but depending on the dosage, the systemic distribution is significantly lower or nonexistent. With a normal application of the BoNT protein according to the prior art, the fluid of the BoNT solution is quickly absorbed and with this absorption, BoNT also gets into the circulation. Since the application of the nucleic acids and the expression of the BoNT are decoupled in time during the transfection, the tissue around the application site has normalized again at the time of the secretion. There is no increased fluid in the extracellular space and the BoNT travels along the muscle membrane to the motor end plates, i.e. to the site of action.

For example, a signal peptide from murine IgG (Kappa) can be used as the secretory signal. The signal sequence is preferably inserted before the luciferase gene (N-terminal). The sequence is

```
(SEQ ID NO 6):
ATGGAGACCGACACCCTGCTGCTGTGGGTGCTGCTGCTGTGGGTGCCCG
GCAGCACCGGCGAC
```

However, this is only an example. Different secretory signals can be used. The choice also depends on the area of application, i.e. the cell to be transfected and the indication.

The invention can therefore be used with or without a secretory signal. When using the corresponding sequence without a secretory signal, it was already completely surprising that the BoNT can get from the cytoplasm of a muscle cell into the synaptic cleft of the motor end plate. In the embodiment which includes a secretory signal, the crucial advantage over the prior art lies above all in the lower systemic distribution with the same or higher dosage compared to the prior art.

In addition to largely avoiding undesirable systemic effects, the risk of antibodies against BoNT being formed by the patient is significantly reduced, since the BoNT is only present to a small extent extracellularly. Most of it is either in the transfected cell that produces the BoNT or already in the target cell of the efferent nerve fiber.

Another advantage is the simpler and cheaper production. A significant cost advantage can be achieved in production, since it is more standardized.

The complex and controversial activity determination does not apply to this recombinant product, which represents a considerable advantage over the prior art. Because animal experiments for batch release would no longer be necessary for the production of the substance according to the invention.

There are completely new options for treating patients. The duration of the expression can be controlled by the choice of the transfection vector and the proportion of the transfected cells can also be varied. In this way, the duration and potency can be influenced. This flexibility is a decisive advantage for the therapeutic application, since it can now be adapted more precisely to the respective patient.

For some therapeutic applications, partial paralysis is advantageous, for example in osteosynthesis, in which it would be advantageous to reduce the muscle tone of the surrounding tissue for the first healing phase. The invention makes now possible such applications for the first time.

The reduced systemic availability not only reduces the toxicity but also the immunogenicity of the BoNT. This is a great advantage for patients with chronic diseases who rely on continuous therapy.

All known serotypes of BoNT or the corresponding nucleic acids can be used for the invention. In other words, the invention relates primarily to nucleic acids for encoding BoNT/A, BoNT/B, BoNT/C, BoNT/D, BoNT/E, BoNT/F and BoNT/G. Preference is given to nucleic acids for encoding BoNT/A, BoNT/B, BoNT/E and BoNT/F. Nucleic acids for encoding BoNT/A, BoNT/B and BoNT/E are particularly preferred.

In addition to the use of different transfection vectors, the gene sequence of the naturally occurring BoNT serotypes can be modified and changed properties of the protein can be achieved, such as changing the duration of action, a different target cell population, a different effect of the translocated light chain or an enhanced release from the muscle cells. An enhanced release from the muscle cell can be done, for example, by inserting a secretory signal.

Furthermore, the protease required to activate the expressed neurotoxin can be additionally expressed or can be introduced after the in vivo transfection by local injection of a small dose. Examples of such proteases include, for example, thrombin or Stuart-Prower factor/factor Xa, which are available as drug products (e.g. Recothrom®, Coagadex®). For this purpose, a recognition motif for the respective protease (thrombin: LVPRGS (SEQ ID NO: 7), factor: Xa LVPRGS (SEQ ID NO: 8)) must be inserted in the BoNT sequence between the light and heavy chain in the linker region. This procedure leads to a further focus of the BoNT effect on the injected area or muscle compartment and thus avoids systemic or distant undesirable side effects of the neurotoxin.

A nucleic acid which comprises a sequence which encodes SEQ ID NO 4 is particularly suitable for this embodiment.

Codon optimization of the BoNT sequence for the expression in human cells is also preferred, as a result of which the efficiency of the expression can be improved.

It is preferred that the nucleic acid comprises a sequence that encodes one of the following protein sequences:

SEQ ID No 1 (BoNT/A Hall Strain):
MPFVNKQFNYKDPVNGVDIAYIKIPNAGQMQPVKAFKIHNKIWVIPERD

TFTNPEEGDLNPPPEAKQVPVSYYDSTYLSTDNEKDNYLKGVTKLFERI

YSTDLGRMLLTSIVRGIPFWGGSTIDTELKVIDTNCINVIQPDGSYRSE

ELNLVIIGPSADIIQFECKSFGHEVLNLTRNGYGSTQYIRFSPDFTFGF

EESLEVDTNPLLGAGKFATDPAVTLAHELIHAGHRLYGIAINPNRVFKV

NTNAYYEMSGLEVSFEELRTFGGHDAKFIDSLQENEFRLYYYNKFKDIA

STLNKAKSIVGTTASLQYMKNVFKEKYLLSEDTSGKFSVDKLKFDKLYK

MLTEIYTEDNFVKFFKVLNRKTYLNFDKAVFKINIVPKVNYTIYDGFNL

RNTNLAANFNGQNTEINNMNFTKLKNFTGLFEFYKLLCVRGIITSKTKS

LDKGYNKALNDLCIKVNNWDLFFSPSEDNFTNDLNKGEEITSDTNIEAA

EENISLDLIQQYYLTFNFDNEPENISIENLSSDIIGQLELMPNIERFPN

GKKYELDKYTMFHYLRAQEFEHGKSRIALTNSVNEALLNPSRVYTFFSS

DYVKKVNKATEAAMFLGWVEQLVYDFTDETSEVSTTDKIADITIIIPYI

GPALNIGNMLYKDDFVGALIFSGAVILLEFIPEIAIPVLGTFALVSYIA

NKVLTVQTIDNALSKRNEKWDEVYKYIVTNWLAKVNTQIDLIRKKMKEA

LENQAEATKAIINYQYNQYTEEEKNNINFNIDDLSSKLNESINKAMINI

NKFLNQCSVSYLMNSMIPYGVKRLEDFDASLKDALLKYIYDNRGTLIGQ

VDRLKDKVNNTLSTDIPFQLSKYVDNQRLLSTFTEYIKNIINISILNLR

YESNHLIDLSRYASKINIGSKVNFDPIDKNQIQLFNLESSKIEVILKNA

IVYNSMYENFSTSFWIRIPKYFNSISLNNEYTIINCMENNSGWKVSLNY

GEIIWTLQDTQEIKQRVVFKYSQMINISDYINRWIFVTITNNRLNNSKI

YINGRLIDQKPISNLGNIHASNNIMFKLDGCRDTHRYIWIKYFNLFDKE

LNEKEIKDLYDNQSNSGILKDFWGDYLQYDKPYYMLNLYDPNKYVDVNN

VGIRGYMYLKGPRGSVMTTNIYLNSSLYRGTKFIIKKYASGNKDNIVRN

NDRVYINVVVKNKEYRLATNASQAGVEKILSALEIPDVGNLSQVVVMKS

KNDQGITNKCKMNLQDNNGNDIGFIGFHQFNNIAKLVASNWYNRQIERS

SRTLGCSWEFIPVDDGWGERPL

SEQ ID No. 2 (BoNT/E):
MPKINSFNYNDPVNDKTILYIKPGGCQQFYKSFNIMKNIWIIPERNVIG

TIPQDFLPPTSLKNGDSSYYDPNYLQSNEEKDRFLKIVTKIFNRINDNL

SGRILLEELSKANPYLGNDNTPDNQFHIGDASAVEIKFSNGNQSILLPN

VIIMGAEPDLFETNSSNISLRNNYMPSNHGFGSIAIVTFSPEYSFRFND

NSMNEFIQDPALTLMHELIHSLHGLYGAKRITTKYTITQQQNPLITNIR

GTNIEEFLTFGGTDLNIITSAQYNDIYTNLLADYKKIASKLSKVQVSNP

QLNPYKDIFQEKYGLDKNASGIYSVNINKFDDIFKKLYSFTEFDLATKF

QVKCRQTYIGQYKYFKLSNLLNNSIYNISEGYNINTLKVNFRGQNTNLN

PRIITQLTGRGLVKKIIRFCKNIVFSKGITKSICIEINNGELFFVASEN

SYNDDNINTPKEIDDTVTSNNNYENDLDQVILNFNSESAPGLSDEKLNL

TIQNDAYIPKYDSNGTSDIEQHDVNELNVFFYLDAQKVPEGENNVNLTS

SIDTALLEQPKIYTFFSSEFINNVNKPVQAALFVSWIQQVLVDFTTEAN

QKSTVDKIADISIVVPYIGLALNIGNEAQKGNFKDALELLGAGILLEFE

-continued

PELLIPTILVFTIKSFLGSSDNKNKVIKAINNALKERDEKWKEVYSFIV

SNWMTKINTQFNKRKEQMYQALQNQVNAIKTIIESKYNSYTLEEKNELT

NKYDIKQIENELNQKVSIAMNNIDRFLTESSISYLMKLINEVKINKLRE

YDENVKTYLLNYIIQHGSILGESQQELNSMVTDTLNNSIPFKLSSYTDD

KILISYFNKFFKRIKSSSVLNMRYKNDKYVDTSGYDSNININGDVYKYP

TNKNQFGIYNDKLSEVNISQNDYIIYDNKYKNFSISFWVRIPNYDNKIV

NVNNEYTIINCMRDNNSGWKVSLNHNEIIWTLQDNAGINQKLAFNYGNA

NGISDYINKWIFVTITNDRLGDSKLYINGNLIDQKSILNLGNIHVSDNI

LFKIVNCSYTRYIGIRYFNIFDKELDETEIQTLYSNEPNTNILKDFWGN

YLLYDKEYYLLNVLKPNNFIDRRKDSTLSINNIRSTILLANRLYSGIKV

KIQRVNNSSTNDNLVRKNDQVYINFVASKTHLFPLYADTATTNKEKTIK

ISSSGNRFNQVVVMNSVGNNCTMNFKNNNGNNIGLLGFKADTVVASTWY

YTHMRDHTNSNGCFWNFISEEHGWQEK

SEQ ID No 3 (BoNT/B):
MPVTINNFNYNDPIDNDNIIMMEPPFARGTGRYYKAFKITDRIWIIPER

YTFGYKPEDFNKSSGIFNRDVCEYYDPDYLNTNDKKNIFFQTLIKLFNR

IKSKPLGEKLLEMIINGIPYLGDRRVPLEEFNTNIASVTVNKLISNPGE

VERKKGIFANLIIFGPGPVLNENETIDIGIQNHFASREGFGGIMQMKFC

PEYVSVFNNVQENKGASIFNRRGYFSDPALILMHELIHVLHGLYGIKVD

DLPIVPNEKKFFMQSTDTIQAEELYTFGGQDPSIISPSTDKSIYDKVLQ

NFRGIVDRLNKVLVCISDPNININIYKNKFKDKYKFVEDSEGKYSIDVE

SFNKLYKSLMLGFTEINIAENYKIKTRASYFSDSLPPVKIKNLLDNEIY

TIEEGFNISDKNMGKEYRGQNKAINKQAYEEISKEHLAVYKIQMCKSVK

VPGICIDVDNENLFFIADKNSFSDDLSKNERVEYNTQNNYIGNDFPINE

LILDTDLISKIELPSENTESLTDFNVDVPVYEKQPAIKKVFTDENTIFQ

YLYSQTFPLNIRDISLTSSFDDALLVSSKVYSFFSMDYIKTANKVVEAG

LFAGWVKQIVDDFVIEANKSSTMDKIADISLIVPYIGLALNVGDETAKG

NFESAFEIAGSSILLEFIPELLIPVVGVFLLESYIDNKNKIIKTIDNAL

TKRVEKWIDMYGLIVAQWLSTVNTQFYTIKEGMYKALNYQAQALEEIIK

YKYNIYSEEEKSNININFNDINSKLNDGINQAMDNINDFINECSVSYLM

KKMIPLAVKKLLDFDNTLKKNLLNYIDENKLYLIGSVEDEKSKVDKYLK

TIIPFDLSTYSNIEILIKIFNKYNSEILNNIILNLRYRDNNLIDLSGYG

AKVEVYDGVKLNDKNQFKLTSSADSKIRVTQNQNIIFNSMFLDFSVSFW

IRIPKYRNDDIQNYIHNEYTIINCMKNNSGWKISIRGNRIIWTLIDING

KTKSVFFEYNIREDISEYINRWFFVTITNNLDNAKIYINGTLESNMDIK

DIGEVIVNGEITFKLDGDVDRTQFIWMKYFSIFNTQLNQSNIKEIYKIQ

SYSEYLKDFWGNPLMYNKEYYMFNAGNKNSYIKLVKDSSVGEILIRSKY

NQNSNYINYRNLYIGEKFIIRRESNSQSINDDIVRKEDYIHLDLVLHHE

EWRVYAYKYFKEQEEKLFLSIISDSNEFYKTIEIKEYDEQPSYSCQLLF

KKDEESTDDIGLIGIHRFYESGVLRKKYKDYFCISKWYLKEVKRKPYKS

NLGCNWQFIPKDEGWTE

-continued

SEQ ID NO 4 (BoNT/A Hall strain with protease recognition motif):
MPFVNKQFNYKDPVNGVDIAYIKIPNAGQMQPVKAFKIHNKIWVIPERD

TFTNPEEGDLNPPPEAKQVPVSYYDSTYLSTDNEKDNYLKGVTKLFERI

YSTDLGRMLLTSIVRGIPFWGGSTIDTELKVIDTNCINVIQPDGSYRSE

ELNLVIIGPSADIIQFECKSFGHEVLNLTRNGYGSTQYIRFSPDFTFGF

EESLEVDTNPLLGAGKFATDPAVTLAHELIHAGHRLYGIAINPNRVFKV

NTNAYYEMSGLEVSFEELRTFGGHDAKFIDSLQENEFRLYYYNKFKDIA

STLNKAKSIVGTTASLQYMKNVFKEKYLLSEDTSGKFSVDKLKFDKLYK

MLTEIYTEDNFVKFFKVLNRKTYLNFDKAVFKINIVPKVNYTIYDGFNL

RNTNLAANFNGQNTEINNMNFTKLKNFTGLFEFYKLLCVRGIITSKTKS

LVPRGSKALNDLCIKVNNWDLFFSPSEDNFTNDLNKGEEITSDTNIEAA

EENISLDLIQQYYLTFNFDNEPENISIENLSSDIIGQLELMPNIERFPN

GKKYELDKYTMFHYLRAQEFEHGKSRIALTNSVNEALLNPSRVYTFFSS

DYVKKVNKATEAAMFLGWVEQLVYDFTDETSEVSTTDKIADITIIIPYI

GPALNIGNMLYKDDFVGALIFSGAVILLEFIPEIAIPVLGTFALVSYIA

NKVLTVQTIDNALSKRNEKWDEVYKYIVTNWLAKVNTQIDLIRKKMKEA

LENQAEATKAIINYQYNQYTEEEKNNINFNIDDLSSKLNESINKAMINI

NKFLNQCSVSYLMNSMIPYGVKRLEDFDASLKDALLKYIYDNRGTLIGQ

VDRLKDKVNNTLSTDIPFQLSKYVDNQRLLSTFTEYIKNIINISILNLR

YESNHLIDLSRYASKINIGSKVNFDPIDKNQIQLFNLESSKIEVILKNA

IVYNSMYENFSTSFWIRIPKYFNSISLNNEYTIINCMENNSGWKVSLNY

GEIIWTLQDTQEIKQRVVFKYSQMINISDYINRWIFVTITNNRLNNSKI

YINGRLIDQKPISNLGNIHASNNIMFKLDGCRDTHRYIWIKYFNLFDKE

LNEKEIKDLYDNQSNSGILKDFWGDYLQYDKPYYMLNLYDPNKYVDVNN

VGIRGYMYLKGPRGSVMTTNIYLNSSLYRGTKFIIKKYASGNKDNIVRN

NDRVYINVVVKNKEYRLATNASQAGVEKILSALEIPDVGNLSQVVVMKS

KNDQGITNKCKMNLQDNNGNDIGFIGFHQFNNIAKLVASNWYNRQIERS

SRTLGCSWEFIPVDDGWGERPL

Also preferred are nucleic acids that comprise a nucleic acid sequence that encode a protein with up to 80% homologous sequence, particularly preferred 90%, very particularly preferred 95%, to SEQ ID No 1, SEQ ID NO 2 or SEQ ID NO 3.

It is further preferred that the nucleic acid of the invention comprises or is complementary to the nucleic acid sequence SEQ ID NO 5 or the corresponding RNA sequence. 80% homologous, particularly preferably 90% homologous, very particularly preferably 95% homologous sequences are also preferred.

SEQ ID NO 5:
ATGCCCTTCGTGAACAAGCAGTTCAACTACAAGGACCCCGTGAACGGCG

TGGACATCGCCTACATCAAGATCCCCAACGCCGGCCAGATGCAGCCCGT

GAAGGCCTTCAAGATCCACAACAAGATCTGGGTGATCCCCGAGCGCGAC

ACCTTCACCAACCCCGAGGAGGGCGACCTGAACCCCCCCCCCGAGGCCA

-continued

AGCAGGTGCCCGTGAGCTACTACGACAGCACCTACCTGAGCACCGACAA

CGAGAAGGACAACTACCTGAAGGGCGTGACCAAGCTGTTCGAGCGCATC

TACAGCACCGACCTGGGCCGCATGCTGCTGACCAGCATCGTGCGCGGCA

TCCCCTTCTGGGGCGGCAGCACCATCGACACCGAGCTGAAGGTGATCGA

CACCAACTGCATCAACGTGATCCAGCCCGACGGCAGCTACCGCAGCGAG

GAGCTGAACCTGGTGATCATCGGCCCCAGCGCCGACATCATCCAGTTCG

AGTGCAAGAGCTTCGGCCACGAGGTGCTGAACCTGACCCGCAACGGCTA

CGGCAGCACCCAGTACATCCGCTTCAGCCCCGACTTCACCTTCGGCTTC

GAGGAGAGCCTGGAGGTGGACACCAACCCCCTGCTGGGCGCCGGCAAGT

TCGCCACCGACCCCGCCGTGACCCTGGCCCACGAGCTGATCCACGCCGG

CCACCGCCTGTACGGCATCGCCATCAACCCCAACCGCGTGTTCAAGGTG

AACACCAACGCCTACTACGAGATGAGCGGCCTGGAGGTGAGCTTCGAGG

AGCTGCGCACCTTCGGCGGCCACGACGCCAAGTTCATCGACAGCCTGCA

GGAGAACGAGTTCCGCCTGTACTACTACAACAAGTTCAAGGACATCGCC

AGCACCCTGAACAAGGCCAAGAGCATCGTGGGCACCACCGCCAGCCTGC

AGTACATGAAGAACGTGTTCAAGGAGAAGTACCTGCTGAGCGAGGACAC

CAGCGGCAAGTTCAGCGTGGACAAGCTGAAGTTCGACAAGCTGTACAAG

ATGCTGACCGAGATCTACACCGAGGACAACTTCGTGAAGTTCTTCAAGG

TGCTGAACCGCAAGACCTACCTGAACTTCGACAAGGCCGTGTTCAAGAT

CAACATCGTGCCCAAGGTGAACTACACCATCTACGACGGCTTCAACCTG

CGCAACACCAACCTGGCCGCCAACTTCAACGGCCAGAACACCGAGATCA

ACAACATGAACTTCACCAAGCTGAAGAACTTCACCGGCCTGTTCGAGTT

CTACAAGCTGCTGTGCGTGCGCGGCATCATCACCAGCAAGACCAAGAGC

CTGGACAAGGGCTACAACAAGGCCCTGAACGACCTGTGCATCAAGGTGA

ACAACTGGGACCTGTTCTTCAGCCCCAGCGAGGACAACTTCACCAACGA

CCTGAACAAGGGCGAGGAGATCACCAGCGACACCAACATCGAGGCCGCC

GAGGAGAACATCAGCCTGGACCTGATCCAGCAGTACTACCTGACCTTCA

ACTTCGACAACGAGCCCGAGAACATCAGCATCGAGAACCTGAGCAGCGA

CATCATCGGCCAGCTGGAGCTGATGCCCAACATCGAGCGCTTCCCCAAC

GGCAAGAAGTACGAGCTGGACAAGTACACCATGTTCCACTACCTGCGCG

CCCAGGAGTTCGAGCACGGCAAGAGCCGCATCGCCCTGACCAACAGCGT

GAACGAGGCCCTGCTGAACCCCAGCCGCGTGTACACCTTCTTCAGCAGC

GACTACGTGAAGAAGGTGAACAAGGCCACCGAGGCCGCCATGTTCCTGG

GCTGGGTGGAGCAGCTGGTGTACGACTTCACCGACGAGACCAGCGAGGT

GAGCACCACCGACAAGATCGCCGACATCACCATCATCATCCCCTACATC

GGCCCCGCCCTGAACATCGGCAACATGCTGTACAAGGACGACTTCGTGG

GCGCCCTGATCTTCAGCGGCGCCGTGATCCTGCTGGAGTTCATCCCCGA

GATCGCCATCCCCGTGCTGGGCACCTTCGCCCTGGTGAGCTACATCGCC

AACAAGGTGCTGACCGTGCAGACCATCGACAACGCCCTGAGCAAGCGCA

ACGAGAAGTGGGACGAGGTGTACAAGTACATCGTGACCAACTGGCTGGC

-continued

```
CAAGGTGAACACCCAGATCGACCTGATCCGCAAGAAGATGAAGGAGGCC

CTGGAGAACCAGGCCGAGGCCACCAAGGCCATCATCAACTACCAGTACA

ACCAGTACACCGAGGAGGAGAAGAACAACATCAACTTCAACATCGACGA

CCTGAGCAGCAAGCTGAACGAGAGCATCAACAAGGCCATGATCAACATC

AACAAGTTCCTGAACCAGTGCAGCGTGAGCTACCTGATGAACAGCATGA

TCCCCTACGGCGTGAAGCGCCTGGAGGACTTCGACGCCAGCCTGAAGGA

CGCCCTGCTGAAGTACATCTACGACAACCGCGGCACCCTGATCGGCCAG

GTGGACCGCCTGAAGGACAAGGTGAACAACACCCTGAGCACCGACATCC

CCTTCCAGCTGAGCAAGTACGTGGACAACCAGCGCCTGCTGAGCACCTT

CACCGAGTACATCAAGAACATCATCAACACCAGCATCCTGAACCTGCGC

TACGAGAGCAACCACCTGATCGACCTGAGCCGCTACGCCAGCAAGATCA

ACATCGGCAGCAAGGTGAACTTCGACCCCATCGACAAGAACCAGATCCA

GCTGTTCAACCTGGAGAGCAGCAAGATCGAGGTGATCCTGAAGAACGCC

ATCGTGTACAACAGCATGTACGAGAACTTCAGCACCAGCTTCTGGATCC

GCATCCCCAAGTACTTCAACAGCATCAGCCTGAACAACGAGTACACCAT

CATCAACTGCATGGAGAACAACAGCGGCTGGAAGGTGAGCCTGAACTAC

GGCGAGATCATCTGGACCCTGCAGGACACCCAGGAGATCAAGCAGCGCG

TGGTGTTCAAGTACAGCCAGATGATCAACATCAGCGACTACATCAACCG

CTGGATCTTCGTGACCATCACCAACAACCGCCTGAACAACAGCAAGATC

TACATCAACGGCCGCCTGATCGACCAGAAGCCCATCAGCAACCTGGGCA

ACATCCACGCCAGCAACAACATCATGTTCAAGCTGGACGGCTGCCGCGA

CACCCACCGCTACATCTGGATCAAGTACTTCAACCTGTTCGACAAGGAG

CTGAACGAGAAGGAGATCAAGGACCTGTACGACAACCAGAGCAACAGCG

GCATCCTGAAGGACTTCTGGGGCGACTACCTGCAGTACGACAAGCCCTA

CTACATGCTGAACCTGTACGACCCCAACAAGTACGTGGACGTGAACAAC

GTGGGCATCCGCGGCTACATGTACCTGAAGGGCCCCCGCGGCAGCGTGA

TGACCACCAACATCTACCTGAACAGCAGCCTGTACCGCGGCACCAAGTT

CATCATCAAGAAGTACGCCAGCGGCAACAAGGACAACATCGTGCGCAAC

AACGACCGCGTGTACATCAACGTGGTGGTGAAGAACAAGGAGTACCGCC

TGGCCACCAACGCCAGCCAGGCCGGCGTGGAGAAGATCCTGAGCGCCCT

GGAGATCCCCGACGTGGGCAACCTGAGCCAGGTGGTGGTGATGAAGAGC

AAGAACGACCAGGGCATCACCAACAAGTGCAAGATGAACCTGCAGGACA

ACAACGGCAACGACATCGGCTTCATCGGCTTCCACCAGTTCAACAACAT

CGCCAAGCTGGTGGCCAGCAACTGGTACAACCGCCAGATCGAGCGCAGC

AGCCGCACCCTGGGCTGCAGCTGGGAGTTCATCCCCGTGGACGACGGCT

GGGGCGAGCGCCCCCTG
```

The present invention also relates to a pharmaceutical composition comprising a nucleic acid according to the invention and a pharmaceutically acceptable carrier and/or excipient.

In a preferred embodiment, the invention also relates to a kit comprising a nucleic acid according to the invention and excipients and optionally a protease.

The pharmaceutical composition is preferably prepared for application into the muscle or skin or a gland.

The teaching according to the application is primarily distinguished by the following features:

- moving away from what is technically common
- new task
- the presence of a long-standing, unresolved, pressing need for a solution to the problem which is solved by the invention
- development of scientific technology went in a different direction.

In particular, the advantageous embodiments of the invention have at least one or more of the advantages listed.

EXAMPLES

The invention is illustrated below with the aid of a few examples and figures, which, however, are not to be understood as limiting the scope.

For our exemplary embodiment we have used mRNA of the BoNT/A Hall strain that encodes a sequence according to SEQ ID No 1. This mRNA was injected into the tibialis muscle of mice at a concentration of 0.4 mg/ml without further additives. Only a very slight paralysis was found (digit abduction score below 1).

In further experiments, various transfection vectors were tested, including a polymer-based transfection reagent (Viromer®) from the manufacturer Lipocalyx. This was set up according to the manufacturer's instructions (Lipocalyx) with the BoNT-mRNA solution. A clear BoNT-mediated paralysis was found.

Figure 3:
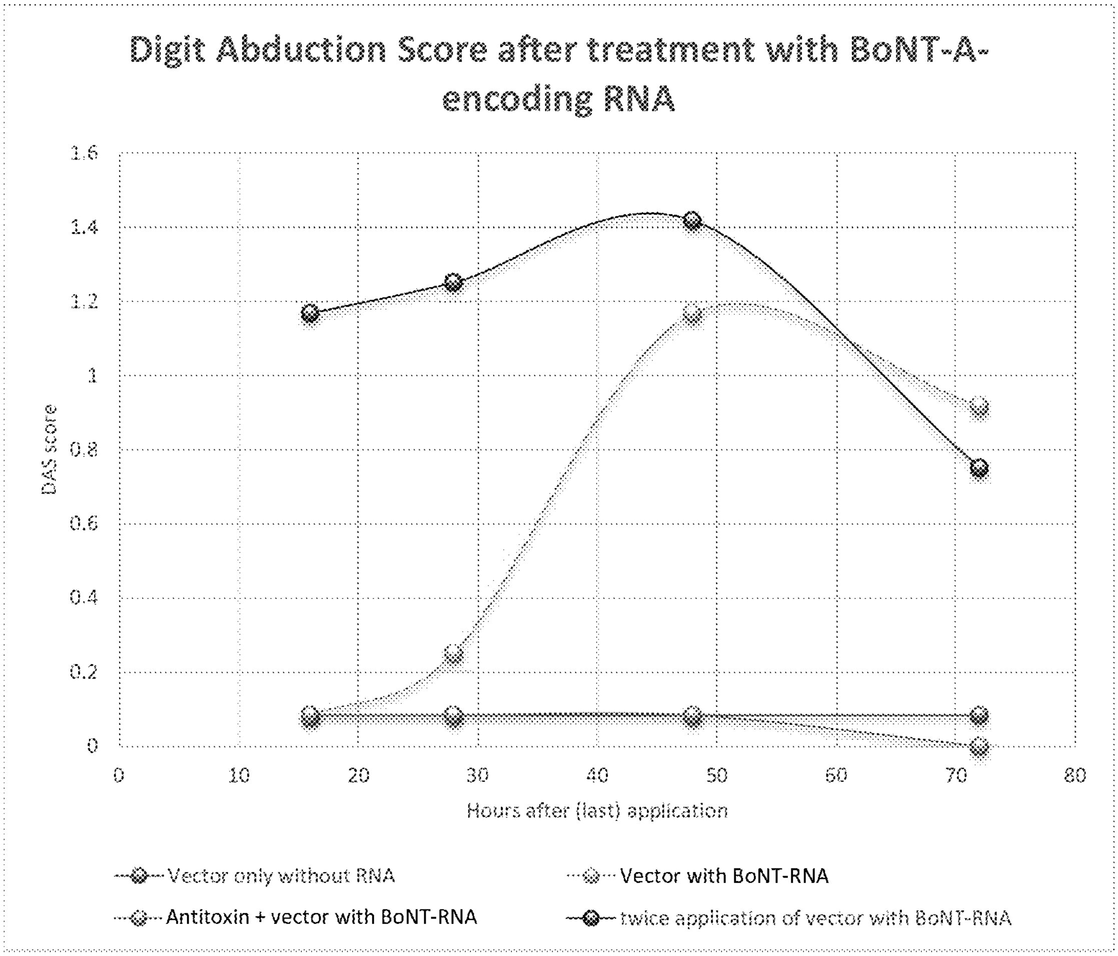
FIG. 3 shows digit abduction score after treatment with BoNT-A-encoding RNA.
Figure 4:
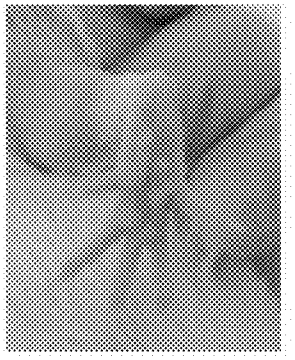
FIG. 4 shows a comparison of a non-paralyzed hind limb of the mouse and a paralyzed hind limb of the mouse. paralyzed by BoNT/A-RNA treatment.
Figure 4:
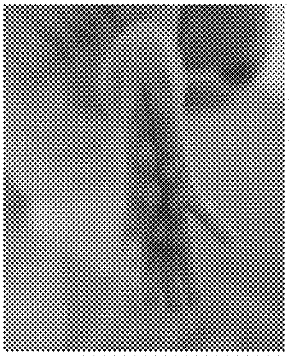

Referring to FIGS. 3 and 4, the digit abduction score is used to evaluate the paralysis mediated by BoNT in a mouse model. The toe-spread reflex of the mouse is used for this purpose. After an injection into the gastrocnemius and or tibialis muscle, the mice, depending on the severity of the paralysis, cannot spread their toes or can only do so to a limited extent. The paralysis is based on a rating system by Aoki et al. Classified from 0=no paralysis up to 4 complete paralysis.

In this study, mice were injected BoNT-A-encoding RNA with a transfection vector into the gastrocnemius and tibialis muscles. In one group, only the transfection vector was applied as a control. In another control group, a BoNT antitoxin was applied beforehand. In the groups treated with BoNT-RNA, one group was treated only once and one group received two treatments at 24-hour intervals. Both control groups showed no paralysis, while the treated groups did not show complete, but clear paralysis.

The invention claimed is:

1. A nucleic acid for use as a drug and/or in therapeutic methods comprising a botulinum neurotoxin (BoNT)-encoding nucleic acid sequence, wherein the BoNT-encoding nucleic acid sequence is modified such that the linker region in the encoded protein between the light and heavy chains comprises a recognition motif for a protease and wherein the BoNT-encoding nucleic acid sequence, excluding the recognition motif for the protease, comprises a sequence according to SEQ ID NO: 1, SEQ ID NO: 2, SEQ ID NO: 3, SEQ ID NO: 4 and SEQ ID NO: 5 or a sequence having 80% sequence identity thereto.

2. A method of treating an organ or muscle in a subject, the method comprising directly applying the nucleic acid according to claim 1 to the organ and/or muscle to be treated.

3. The method according to claim 2, wherein the subject is treated for spasticity, dystonia, saliva leakage, movement disorders, impaired muscle activity, osteosynthesis and/or hyperhydrosis.

4. A method of transfecting skeletal muscle cells, smooth muscle cells, smooth muscle cells of the glands or the skin and/or other skin cells, the method comprising transfecting the muscle cells, smooth muscle cells, smooth muscle cells of the glands or the skin and/or other skin cells with the nucleic acid according to claim 1.

5. The nucleic acid according to claim 1, wherein said nucleic acid is a DNA or RNA.

6. The nucleic acid according to claim 1, wherein the BoNT-encoding nucleic acid sequence encodes BoNT/A, BoNT/B, BoNT/C, BoNT/D, BoNT/E, BoNT/F or BoNT/G.

7. The nucleic acid according to claim 1, additionally comprising a secretory signal-encoding sequence.

8. The nucleic acid according to claim 1 additionally comprising a scaffold/matrix attachment region (S/MAR) element.

9. A method of cosmetically treating a subject, the method comprising administering a nucleic acid according to claim 1 to the subject, thereby cosmetically treating the subject.

10. The method of claim 9, wherein said botulinum neurotoxin expressed in vivo is activated by a simultaneously or subsequently injected protease.

11. The method according to claim 9, wherein the nucleic acid additionally comprising a secretory signal-encoding sequence.

12. The method according to claim 9, wherein the nucleic acid additionally comprising a S/MAR element.

13. A pharmaceutical composition comprising a nucleic acid according to claim 1 and a pharmaceutically acceptable carrier and/or excipient.

14. The nucleic acid according to claim 1, wherein the recognition motif for the respective protease is LVPRGS (SEQ ID NO: 7).

* * * * *

SEQUENCE LISTING

```
<160> NUMBER OF SEQ ID NOS: 8

<210> SEQ ID NO 1
```

-continued

<211> LENGTH: 1296
<212> TYPE: PRT
<213> ORGANISM: Clostridium botulinum

<400> SEQUENCE: 1

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
```

-continued

```
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815
```

-continued

```
Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
        915                 920                 925

Lys Asn Ala Ile Val Tyr Asn Ser Met Tyr Glu Asn Phe Ser Thr Ser
    930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
            980                 985                 990

Ile Lys Gln Arg Val Val Phe Lys  Tyr Ser Gln Met Ile  Asn Ile Ser
        995                 1000                 1005

Asp Tyr  Ile Asn Arg Trp Ile  Phe Val Thr Ile Thr  Asn Asn Arg
    1010                 1015                 1020

Leu Asn  Asn Ser Lys Ile Tyr  Ile Asn Gly Arg Leu  Ile Asp Gln
    1025                 1030                 1035

Lys Pro  Ile Ser Asn Leu Gly  Asn Ile His Ala Ser  Asn Asn Ile
    1040                 1045                 1050

Met Phe  Lys Leu Asp Gly Cys  Arg Asp Thr His Arg  Tyr Ile Trp
    1055                 1060                 1065

Ile Lys  Tyr Phe Asn Leu Phe  Asp Lys Glu Leu Asn  Glu Lys Glu
    1070                 1075                 1080

Ile Lys  Asp Leu Tyr Asp Asn  Gln Ser Asn Ser Gly  Ile Leu Lys
    1085                 1090                 1095

Asp Phe  Trp Gly Asp Tyr Leu  Gln Tyr Asp Lys Pro  Tyr Tyr Met
    1100                 1105                 1110

Leu Asn  Leu Tyr Asp Pro Asn  Lys Tyr Val Asp Val  Asn Asn Val
    1115                 1120                 1125

Gly Ile  Arg Gly Tyr Met Tyr  Leu Lys Gly Pro Arg  Gly Ser Val
    1130                 1135                 1140

Met Thr  Thr Asn Ile Tyr Leu  Asn Ser Ser Leu Tyr  Arg Gly Thr
    1145                 1150                 1155

Lys Phe  Ile Ile Lys Lys Tyr  Ala Ser Gly Asn Lys  Asp Asn Ile
    1160                 1165                 1170

Val Arg  Asn Asn Asp Arg Val  Tyr Ile Asn Val Val  Val Lys Asn
    1175                 1180                 1185

Lys Glu  Tyr Arg Leu Ala Thr  Asn Ala Ser Gln Ala  Gly Val Glu
    1190                 1195                 1200

Lys Ile  Leu Ser Ala Leu Glu  Ile Pro Asp Val Gly  Asn Leu Ser
    1205                 1210                 1215
```

-continued

Gln Val Val Val Met Lys Ser Lys Asn Asp Gln Gly Ile Thr Asn
1220 1225 1230

Lys Cys Lys Met Asn Leu Gln Asp Asn Asn Gly Asn Asp Ile Gly
1235 1240 1245

Phe Ile Gly Phe His Gln Phe Asn Asn Ile Ala Lys Leu Val Ala
1250 1255 1260

Ser Asn Trp Tyr Asn Arg Gln Ile Glu Arg Ser Ser Arg Thr Leu
1265 1270 1275

Gly Cys Ser Trp Glu Phe Ile Pro Val Asp Asp Gly Trp Gly Glu
1280 1285 1290

Arg Pro Leu
1295

<210> SEQ ID NO 2
<211> LENGTH: 1252
<212> TYPE: PRT
<213> ORGANISM: Clostridium botulinum

<400> SEQUENCE: 2

Met Pro Lys Ile Asn Ser Phe Asn Tyr Asn Asp Pro Val Asn Asp Lys
1 5 10 15

Thr Ile Leu Tyr Ile Lys Pro Gly Gly Cys Gln Gln Phe Tyr Lys Ser
20 25 30

Phe Asn Ile Met Lys Asn Ile Trp Ile Ile Pro Glu Arg Asn Val Ile
35 40 45

Gly Thr Ile Pro Gln Asp Phe Leu Pro Pro Thr Ser Leu Lys Asn Gly
50 55 60

Asp Ser Ser Tyr Tyr Asp Pro Asn Tyr Leu Gln Ser Asn Glu Glu Lys
65 70 75 80

Asp Arg Phe Leu Lys Ile Val Thr Lys Ile Phe Asn Arg Ile Asn Asp
85 90 95

Asn Leu Ser Gly Arg Ile Leu Leu Glu Glu Leu Ser Lys Ala Asn Pro
100 105 110

Tyr Leu Gly Asn Asp Asn Thr Pro Asp Asn Gln Phe His Ile Gly Asp
115 120 125

Ala Ser Ala Val Glu Ile Lys Phe Ser Asn Gly Asn Gln Ser Ile Leu
130 135 140

Leu Pro Asn Val Ile Ile Met Gly Ala Glu Pro Asp Leu Phe Glu Thr
145 150 155 160

Asn Ser Ser Asn Ile Ser Leu Arg Asn Asn Tyr Met Pro Ser Asn His
165 170 175

Gly Phe Gly Ser Ile Ala Ile Val Thr Phe Ser Pro Glu Tyr Ser Phe
180 185 190

Arg Phe Asn Asp Asn Ser Met Asn Glu Phe Ile Gln Asp Pro Ala Leu
195 200 205

Thr Leu Met His Glu Leu Ile His Ser Leu His Gly Leu Tyr Gly Ala
210 215 220

Lys Arg Ile Thr Thr Lys Tyr Thr Ile Thr Gln Gln Gln Asn Pro Leu
225 230 235 240

Ile Thr Asn Ile Arg Gly Thr Asn Ile Glu Glu Phe Leu Thr Phe Gly
245 250 255

Gly Thr Asp Leu Asn Ile Ile Thr Ser Ala Gln Tyr Asn Asp Ile Tyr
260 265 270

Thr Asn Leu Leu Ala Asp Tyr Lys Lys Ile Ala Ser Lys Leu Ser Lys
275 280 285

-continued

```
Val Gln Val Ser Asn Pro Gln Leu Asn Pro Tyr Lys Asp Ile Phe Gln
    290                 295                 300

Glu Lys Tyr Gly Leu Asp Lys Asn Ala Ser Gly Ile Tyr Ser Val Asn
305                 310                 315                 320

Ile Asn Lys Phe Asp Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asn Ser Ile
        355                 360                 365

Tyr Asn Ile Ser Glu Gly Tyr Asn Ile Asn Thr Leu Lys Val Asn Phe
    370                 375                 380

Arg Gly Gln Asn Thr Asn Leu Asn Pro Arg Ile Ile Thr Gln Leu Thr
385                 390                 395                 400

Gly Arg Gly Leu Val Lys Lys Ile Ile Arg Phe Cys Lys Asn Ile Val
                405                 410                 415

Phe Ser Lys Gly Ile Thr Lys Ser Ile Cys Ile Glu Ile Asn Asn Gly
            420                 425                 430

Glu Leu Phe Phe Val Ala Ser Glu Asn Ser Tyr Asn Asp Asp Asn Ile
        435                 440                 445

Asn Thr Pro Lys Glu Ile Asp Asp Thr Val Thr Ser Asn Asn Asn Tyr
    450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
                485                 490                 495

Tyr Ile Pro Lys Tyr Asp Ser Asn Gly Thr Ser Asp Ile Glu Gln His
            500                 505                 510

Asp Val Asn Glu Leu Asn Val Phe Phe Tyr Leu Asp Ala Gln Lys Val
        515                 520                 525

Pro Glu Gly Glu Asn Asn Val Asn Leu Thr Ser Ser Ile Asp Thr Ala
    530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Ser Trp Ile
                565                 570                 575

Gln Gln Val Leu Val Asp Phe Thr Thr Glu Ala Asn Gln Lys Ser Thr
            580                 585                 590

Val Asp Lys Ile Ala Asp Ile Ser Ile Val Val Pro Tyr Ile Gly Leu
        595                 600                 605

Ala Leu Asn Ile Gly Asn Glu Ala Gln Lys Gly Asn Phe Lys Asp Ala
    610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
                645                 650                 655

Ser Asp Asn Lys Asn Lys Val Ile Lys Ala Ile Asn Asn Ala Leu Lys
            660                 665                 670

Glu Arg Asp Glu Lys Trp Lys Glu Val Tyr Ser Phe Ile Val Ser Asn
        675                 680                 685

Trp Met Thr Lys Ile Asn Thr Gln Phe Asn Lys Arg Lys Glu Gln Met
    690                 695                 700
```

-continued

```
Tyr Gln Ala Leu Gln Asn Gln Val Asn Ala Ile Lys Thr Ile Ile Glu
705                 710                 715                 720

Ser Lys Tyr Asn Ser Tyr Thr Leu Glu Glu Lys Asn Glu Leu Thr Asn
                725                 730                 735

Lys Tyr Asp Ile Lys Gln Ile Glu Asn Glu Leu Asn Gln Lys Val Ser
            740                 745                 750

Ile Ala Met Asn Asn Ile Asp Arg Phe Leu Thr Glu Ser Ser Ile Ser
        755                 760                 765

Tyr Leu Met Lys Leu Ile Asn Glu Val Lys Ile Asn Lys Leu Arg Glu
    770                 775                 780

Tyr Asp Glu Asn Val Lys Thr Tyr Leu Leu Asn Tyr Ile Ile Gln His
785                 790                 795                 800

Gly Ser Ile Leu Gly Glu Ser Gln Gln Glu Leu Asn Ser Met Val Thr
                805                 810                 815

Asp Thr Leu Asn Asn Ser Ile Pro Phe Lys Leu Ser Ser Tyr Thr Asp
            820                 825                 830

Asp Lys Ile Leu Ile Ser Tyr Phe Asn Lys Phe Phe Lys Arg Ile Lys
        835                 840                 845

Ser Ser Ser Val Leu Asn Met Arg Tyr Lys Asn Asp Lys Tyr Val Asp
    850                 855                 860

Thr Ser Gly Tyr Asp Ser Asn Ile Asn Ile Asn Gly Asp Val Tyr Lys
865                 870                 875                 880

Tyr Pro Thr Asn Lys Asn Gln Phe Gly Ile Tyr Asn Asp Lys Leu Ser
                885                 890                 895

Glu Val Asn Ile Ser Gln Asn Asp Tyr Ile Ile Tyr Asp Asn Lys Tyr
            900                 905                 910

Lys Asn Phe Ser Ile Ser Phe Trp Val Arg Ile Pro Asn Tyr Asp Asn
        915                 920                 925

Lys Ile Val Asn Val Asn Asn Glu Tyr Thr Ile Ile Asn Cys Met Arg
    930                 935                 940

Asp Asn Asn Ser Gly Trp Lys Val Ser Leu Asn His Asn Glu Ile Ile
945                 950                 955                 960

Trp Thr Leu Gln Asp Asn Ala Gly Ile Asn Gln Lys Leu Ala Phe Asn
                965                 970                 975

Tyr Gly Asn Ala Asn Gly Ile Ser Asp Tyr Ile Asn Lys Trp Ile Phe
            980                 985                 990

Val Thr Ile Thr Asn Asp Arg Leu  Gly Asp Ser Lys Leu  Tyr Ile Asn
        995                 1000                 1005

Gly Asn  Leu Ile Asp Gln Lys  Ser Ile Leu Asn Leu  Gly Asn Ile
    1010                 1015                 1020

His Val  Ser Asp Asn Ile Leu  Phe Lys Ile Val Asn  Cys Ser Tyr
    1025                 1030                 1035

Thr Arg  Tyr Ile Gly Ile Arg  Tyr Phe Asn Ile Phe  Asp Lys Glu
    1040                 1045                 1050

Leu Asp  Glu Thr Glu Ile Gln  Thr Leu Tyr Ser Asn  Glu Pro Asn
    1055                 1060                 1065

Thr Asn  Ile Leu Lys Asp Phe  Trp Gly Asn Tyr Leu  Leu Tyr Asp
    1070                 1075                 1080

Lys Glu  Tyr Tyr Leu Leu Asn  Val Leu Lys Pro Asn  Asn Phe Ile
    1085                 1090                 1095

Asp Arg  Arg Lys Asp Ser Thr  Leu Ser Ile Asn Asn  Ile Arg Ser
    1100                 1105                 1110

Thr Ile  Leu Leu Ala Asn Arg  Leu Tyr Ser Gly Ile  Lys Val Lys
```

-continued 1115 1120 1125

Ile Gln Arg Val Asn Asn Ser Ser Thr Asn Asp Asn Leu Val Arg
1130 1135 1140

Lys Asn Asp Gln Val Tyr Ile Asn Phe Val Ala Ser Lys Thr His
1145 1150 1155

Leu Phe Pro Leu Tyr Ala Asp Thr Ala Thr Thr Asn Lys Glu Lys
1160 1165 1170

Thr Ile Lys Ile Ser Ser Ser Gly Asn Arg Phe Asn Gln Val Val
1175 1180 1185

Val Met Asn Ser Val Gly Asn Asn Cys Thr Met Asn Phe Lys Asn
1190 1195 1200

Asn Asn Gly Asn Asn Ile Gly Leu Leu Gly Phe Lys Ala Asp Thr
1205 1210 1215

Val Val Ala Ser Thr Trp Tyr Tyr Thr His Met Arg Asp His Thr
1220 1225 1230

Asn Ser Asn Gly Cys Phe Trp Asn Phe Ile Ser Glu Glu His Gly
1235 1240 1245

Trp Gln Glu Lys
1250

<210> SEQ ID NO 3
<211> LENGTH: 1291
<212> TYPE: PRT
<213> ORGANISM: Clostridium botulinum

<400> SEQUENCE: 3

Met Pro Val Thr Ile Asn Asn Phe Asn Tyr Asn Asp Pro Ile Asp Asn
1 5 10 15

Asp Asn Ile Ile Met Met Glu Pro Pro Phe Ala Arg Gly Thr Gly Arg
20 25 30

Tyr Tyr Lys Ala Phe Lys Ile Thr Asp Arg Ile Trp Ile Ile Pro Glu
35 40 45

Arg Tyr Thr Phe Gly Tyr Lys Pro Glu Asp Phe Asn Lys Ser Ser Gly
50 55 60

Ile Phe Asn Arg Asp Val Cys Glu Tyr Tyr Asp Pro Asp Tyr Leu Asn
65 70 75 80

Thr Asn Asp Lys Lys Asn Ile Phe Phe Gln Thr Leu Ile Lys Leu Phe
85 90 95

Asn Arg Ile Lys Ser Lys Pro Leu Gly Glu Lys Leu Leu Glu Met Ile
100 105 110

Ile Asn Gly Ile Pro Tyr Leu Gly Asp Arg Arg Val Pro Leu Glu Glu
115 120 125

Phe Asn Thr Asn Ile Ala Ser Val Thr Val Asn Lys Leu Ile Ser Asn
130 135 140

Pro Gly Glu Val Glu Arg Lys Lys Gly Ile Phe Ala Asn Leu Ile Ile
145 150 155 160

Phe Gly Pro Gly Pro Val Leu Asn Glu Asn Glu Thr Ile Asp Ile Gly
165 170 175

Ile Gln Asn His Phe Ala Ser Arg Glu Gly Phe Gly Gly Ile Met Gln
180 185 190

Met Lys Phe Cys Pro Glu Tyr Val Ser Val Phe Asn Asn Val Gln Glu
195 200 205

Asn Lys Gly Ala Ser Ile Phe Asn Arg Arg Gly Tyr Phe Ser Asp Pro
210 215 220

-continued

```
Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Thr Ile Gln Ala Glu Glu Leu Tyr Thr Phe
            260                 265                 270

Gly Gly Gln Asp Pro Ser Ile Ile Ser Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asn Lys Leu Tyr Lys Ser Leu
            340                 345                 350

Met Leu Gly Phe Thr Glu Ile Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asn Met Gly Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Val Pro Gly Ile Cys Ile Asp
        435                 440                 445

Val Asp Asn Glu Asn Leu Phe Phe Ile Ala Asp Lys Asn Ser Phe Ser
    450                 455                 460

Asp Asp Leu Ser Lys Asn Glu Arg Val Glu Tyr Asn Thr Gln Asn Asn
465                 470                 475                 480

Tyr Ile Gly Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
        515                 520                 525

Lys Val Phe Thr Asp Glu Asn Thr Ile Phe Gln Tyr Leu Tyr Ser Gln
    530                 535                 540

Thr Phe Pro Leu Asn Ile Arg Asp Ile Ser Leu Thr Ser Ser Phe Asp
545                 550                 555                 560

Asp Ala Leu Leu Val Ser Ser Lys Val Tyr Ser Phe Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asp Asp Phe Val Ile Glu Ala Asn Lys Ser
        595                 600                 605

Ser Thr Met Asp Lys Ile Ala Asp Ile Ser Leu Ile Val Pro Tyr Ile
    610                 615                 620

Gly Leu Ala Leu Asn Val Gly Asp Glu Thr Ala Lys Gly Asn Phe Glu
625                 630                 635                 640

Ser Ala Phe Glu Ile Ala Gly Ser Ser Ile Leu Leu Glu Phe Ile Pro
```

-continued

```
                645                 650                 655

Glu Leu Leu Ile Pro Val Val Gly Val Phe Leu Leu Glu Ser Tyr Ile
            660                 665                 670

Asp Asn Lys Asn Lys Ile Ile Lys Thr Ile Asp Asn Ala Leu Thr Lys
        675                 680                 685

Arg Val Glu Lys Trp Ile Asp Met Tyr Gly Leu Ile Val Ala Gln Trp
    690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Lys Tyr Asn Ile Tyr Ser Glu Glu Glu Lys Ser Asn Ile Asn Ile Asn
            740                 745                 750

Phe Asn Asp Ile Asn Ser Lys Leu Asn Asp Gly Ile Asn Gln Ala Met
        755                 760                 765

Asp Asn Ile Asn Asp Phe Ile Asn Glu Cys Ser Val Ser Tyr Leu Met
    770                 775                 780

Lys Lys Met Ile Pro Leu Ala Val Lys Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Val Glu Asp Glu Lys Ser Lys Val Asp Lys Tyr Leu
            820                 825                 830

Lys Thr Ile Ile Pro Phe Asp Leu Ser Thr Tyr Ser Asn Ile Glu Ile
        835                 840                 845

Leu Ile Lys Ile Phe Asn Lys Tyr Asn Ser Glu Ile Leu Asn Asn Ile
    850                 855                 860

Ile Leu Asn Leu Arg Tyr Arg Asp Asn Asn Leu Ile Asp Leu Ser Gly
865                 870                 875                 880

Tyr Gly Ala Lys Val Glu Val Tyr Asp Gly Val Lys Leu Asn Asp Lys
                885                 890                 895

Asn Gln Phe Lys Leu Thr Ser Ser Ala Asp Ser Lys Ile Arg Val Thr
            900                 905                 910

Gln Asn Gln Asn Ile Ile Phe Asn Ser Met Phe Leu Asp Phe Ser Val
        915                 920                 925

Ser Phe Trp Ile Arg Ile Pro Lys Tyr Arg Asn Asp Asp Ile Gln Asn
    930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975

Asp Ile Asn Gly Lys Thr Lys Ser Val Phe Phe Glu Tyr Asn Ile Arg
            980                 985                 990

Glu Asp Ile Ser Glu Tyr Ile Asn  Arg Trp Phe Phe Val  Thr Ile Thr
        995                 1000                1005

Asn Asn  Leu Asp Asn Ala Lys  Ile Tyr Ile Asn Gly  Thr Leu Glu
    1010                1015                1020

Ser Asn  Met Asp Ile Lys Asp  Ile Gly Glu Val Ile  Val Asn Gly
    1025                1030                1035

Glu Ile  Thr Phe Lys Leu Asp  Gly Asp Val Asp Arg  Thr Gln Phe
    1040                1045                1050

Ile Trp  Met Lys Tyr Phe Ser  Ile Phe Asn Thr Gln  Leu Asn Gln
    1055                1060                1065
```

```
Ser Asn  Ile Lys Glu Ile Tyr  Lys Ile Gln Ser Tyr  Ser Glu Tyr
    1070                 1075                 1080

Leu Lys  Asp Phe Trp Gly Asn  Pro Leu Met Tyr Asn  Lys Glu Tyr
    1085                 1090                 1095

Tyr Met  Phe Asn Ala Gly Asn  Lys Asn Ser Tyr Ile  Lys Leu Val
    1100                 1105                 1110

Lys Asp  Ser Ser Val Gly Glu  Ile Leu Ile Arg Ser  Lys Tyr Asn
    1115                 1120                 1125

Gln Asn  Ser Asn Tyr Ile Asn  Tyr Arg Asn Leu Tyr  Ile Gly Glu
    1130                 1135                 1140

Lys Phe  Ile Ile Arg Arg Glu  Ser Asn Ser Gln Ser  Ile Asn Asp
    1145                 1150                 1155

Asp Ile  Val Arg Lys Glu Asp  Tyr Ile His Leu Asp  Leu Val Leu
    1160                 1165                 1170

His His  Glu Glu Trp Arg Val  Tyr Ala Tyr Lys Tyr  Phe Lys Glu
    1175                 1180                 1185

Gln Glu  Glu Lys Leu Phe Leu  Ser Ile Ile Ser Asp  Ser Asn Glu
    1190                 1195                 1200

Phe Tyr  Lys Thr Ile Glu Ile  Lys Glu Tyr Asp Glu  Gln Pro Ser
    1205                 1210                 1215

Tyr Ser  Cys Gln Leu Leu Phe  Lys Lys Asp Glu Glu  Ser Thr Asp
    1220                 1225                 1230

Asp Ile  Gly Leu Ile Gly Ile  His Arg Phe Tyr Glu  Ser Gly Val
    1235                 1240                 1245

Leu Arg  Lys Lys Tyr Lys Asp  Tyr Phe Cys Ile Ser  Lys Trp Tyr
    1250                 1255                 1260

Leu Lys  Glu Val Lys Arg Lys  Pro Tyr Lys Ser Asn  Leu Gly Cys
    1265                 1270                 1275

Asn Trp  Gln Phe Ile Pro Lys  Asp Glu Gly Trp Thr  Glu
    1280                 1285                 1290


<210> SEQ ID NO 4
<211> LENGTH: 1296
<212> TYPE: PRT
<213> ORGANISM: Clostridium botulinum

<400> SEQUENCE: 4

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
```

-continued

```
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Val Pro Arg Gly Ser Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560
```

-continued

```
His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
        915                 920                 925

Lys Asn Ala Ile Val Tyr Asn Ser Met Tyr Glu Asn Phe Ser Thr Ser
    930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975
```

-continued

```
Ser Leu Asn Tyr Gly Glu Ile Ile Trp Thr Leu Gln Asp Thr Gln Glu
            980                 985                 990

Ile Lys Gln Arg Val Val Phe Lys  Tyr Ser Gln Met Ile  Asn Ile Ser
        995                 1000                 1005

Asp Tyr  Ile Asn Arg Trp Ile  Phe Val Thr Ile Thr  Asn Asn Arg
    1010                 1015                 1020

Leu Asn  Asn Ser Lys Ile Tyr  Ile Asn Gly Arg Leu  Ile Asp Gln
    1025                 1030                 1035

Lys Pro  Ile Ser Asn Leu Gly  Asn Ile His Ala Ser  Asn Asn Ile
    1040                 1045                 1050

Met Phe  Lys Leu Asp Gly Cys  Arg Asp Thr His Arg  Tyr Ile Trp
    1055                 1060                 1065

Ile Lys  Tyr Phe Asn Leu Phe  Asp Lys Glu Leu Asn  Glu Lys Glu
    1070                 1075                 1080

Ile Lys  Asp Leu Tyr Asp Asn  Gln Ser Asn Ser Gly  Ile Leu Lys
    1085                 1090                 1095

Asp Phe  Trp Gly Asp Tyr Leu  Gln Tyr Asp Lys Pro  Tyr Tyr Met
    1100                 1105                 1110

Leu Asn  Leu Tyr Asp Pro Asn  Lys Tyr Val Asp Val  Asn Asn Val
    1115                 1120                 1125

Gly Ile  Arg Gly Tyr Met Tyr  Leu Lys Gly Pro Arg  Gly Ser Val
    1130                 1135                 1140

Met Thr  Thr Asn Ile Tyr Leu  Asn Ser Ser Leu Tyr  Arg Gly Thr
    1145                 1150                 1155

Lys Phe  Ile Ile Lys Lys Tyr  Ala Ser Gly Asn Lys  Asp Asn Ile
    1160                 1165                 1170

Val Arg  Asn Asn Asp Arg Val  Tyr Ile Asn Val Val  Val Lys Asn
    1175                 1180                 1185

Lys Glu  Tyr Arg Leu Ala Thr  Asn Ala Ser Gln Ala  Gly Val Glu
    1190                 1195                 1200

Lys Ile  Leu Ser Ala Leu Glu  Ile Pro Asp Val Gly  Asn Leu Ser
    1205                 1210                 1215

Gln Val  Val Val Met Lys Ser  Lys Asn Asp Gln Gly  Ile Thr Asn
    1220                 1225                 1230

Lys Cys  Lys Met Asn Leu Gln  Asp Asn Asn Gly Asn  Asp Ile Gly
    1235                 1240                 1245

Phe Ile  Gly Phe His Gln Phe  Asn Asn Ile Ala Lys  Leu Val Ala
    1250                 1255                 1260

Ser Asn  Trp Tyr Asn Arg Gln  Ile Glu Arg Ser Ser  Arg Thr Leu
    1265                 1270                 1275

Gly Cys  Ser Trp Glu Phe Ile  Pro Val Asp Asp Gly  Trp Gly Glu
    1280                 1285                 1290

Arg Pro  Leu
    1295


<210> SEQ ID NO 5
<211> LENGTH: 3888
<212> TYPE: DNA
<213> ORGANISM: Artificial Sequence
<220> FEATURE:
<223> OTHER INFORMATION: Codon optimized DNA-Sequence for Expression in
      human cells

<400> SEQUENCE: 5

atgcccttcg tgaacaagca gttcaactac aaggaccccg tgaacggcgt ggacatcgcc     60
```

-continued

```
tacatcaaga tccccaacgc cggccagatg cagcccgtga aggccttcaa gatccacaac    120
aagatctggg tgatccccga gcgcgacacc ttcaccaacc ccgaggaggg cgacctgaac    180
cccccccccg aggccaagca ggtgcccgtg agctactacg acagcaccta cctgagcacc    240
gacaacgaga aggacaacta cctgaagggc gtgaccaagc tgttcgagcg catctacagc    300
accgacctgg gccgcatgct gctgaccagc atcgtgcgcg gcatcccctt ctggggcggc    360
agcaccatcg acaccgagct gaaggtgatc gacaccaact gcatcaacgt gatccagccc    420
gacggcagct accgcagcga ggagctgaac ctggtgatca tcggccccag cgccgacatc    480
atccagttcg agtgcaagag cttcggccac gaggtgctga acctgacccg caacggctac    540
ggcagcaccc agtacatccg cttcagcccc gacttcacct tcggcttcga ggagagcctg    600
gaggtggaca ccaaccccct gctgggcgcc ggcaagttcg ccaccgaccc cgccgtgacc    660
ctggcccacg agctgatcca cgccggccac cgcctgtacg gcatcgccat caaccccaac    720
cgcgtgttca aggtgaacac caacgcctac tacgagatga gcggcctgga ggtgagcttc    780
gaggagctgc gcaccttcgg cggccacgac gccaagttca tcgacagcct gcaggagaac    840
gagttccgcc tgtactacta caacaagttc aaggacatcg ccagcaccct gaacaaggcc    900
aagagcatcg tgggcaccac cgccagcctg cagtacatga agaacgtgtt caaggagaag    960
tacctgctga gcgaggacac cagcggcaag ttcagcgtgg acaagctgaa gttcgacaag   1020
ctgtacaaga tgctgaccga gatctacacc gaggacaact tcgtgaagtt cttcaaggtg   1080
ctgaaccgca agacctacct gaacttcgac aaggccgtgt tcaagatcaa catcgtgccc   1140
aaggtgaact acaccatcta cgacggcttc aacctgcgca acaccaacct ggccgccaac   1200
ttcaacggcc agaacaccga gatcaacaac atgaacttca ccaagctgaa gaacttcacc   1260
ggcctgttcg agttctacaa gctgctgtgc gtgcgcggca tcatcaccag caagaccaag   1320
agcctggaca agggctacaa caaggccctg aacgacctgt gcatcaaggt gaacaactgg   1380
gacctgttct tcagccccag cgaggacaac ttcaccaacg acctgaacaa gggcgaggag   1440
atcaccagcg acaccaacat cgaggccgcc gaggagaaca tcagcctgga cctgatccag   1500
cagtactacc tgaccttcaa cttcgacaac gagcccgaga acatcagcat cgagaacctg   1560
agcagcgaca tcatcggcca gctggagctg atgcccaaca tcgagcgctt ccccaacggc   1620
aagaagtacg agctggacaa gtacaccatg ttccactacc tgcgcgccca ggagttcgag   1680
cacggcaaga gccgcatcgc cctgaccaac agcgtgaacg aggccctgct gaaccccagc   1740
cgcgtgtaca ccttcttcag cagcgactac gtgaagaagg tgaacaaggc caccgaggcc   1800
gccatgttcc tgggctgggt ggagcagctg gtgtacgact tcaccgacga gaccagcgag   1860
gtgagcacca ccgacaagat cgccgacatc accatcatca tcccctacat cggccccgcc   1920
ctgaacatcg gcaacatgct gtacaaggac gacttcgtgg gcgccctgat cttcagcggc   1980
gccgtgatcc tgctggagtt catccccgag atcgccatcc ccgtgctggg caccttcgcc   2040
ctggtgagct acatcgccaa caaggtgctg accgtgcaga ccatcgacaa cgccctgagc   2100
aagcgcaacg agaagtggga cgaggtgtac aagtacatcg tgaccaactg gctggccaag   2160
gtgaacaccc agatcgacct gatccgcaag aagatgaagg aggccctgga gaaccaggcc   2220
gaggccacca aggccatcat caactaccag tacaaccagt acaccgagga ggagaagaac   2280
aacatcaact tcaacatcga cgacctgagc agcaagctga acgagagcat caacaaggcc   2340
atgatcaaca tcaacaagtt cctgaaccag tgcagcgtga gctacctgat gaacagcatg   2400
atcccctacg gcgtgaagcg cctggaggac ttcgacgcca gcctgaagga cgccctgctg   2460
```

```
aagtacatct acgacaaccg cggcaccctg atcggccagg tggaccgcct gaaggacaag   2520

gtgaacaaca ccctgagcac cgacatcccc ttccagctga gcaagtacgt ggacaaccag   2580

cgcctgctga gcaccttcac cgagtacatc aagaacatca tcaacaccag catcctgaac   2640

ctgcgctacg agagcaacca cctgatcgac ctgagccgct acgccagcaa gatcaacatc   2700

ggcagcaagg tgaacttcga ccccatcgac aagaaccaga tccagctgtt caacctggag   2760

agcagcaaga tcgaggtgat cctgaagaac gccatcgtgt acaacagcat gtacgagaac   2820

ttcagcacca gcttctggat ccgcatcccc aagtacttca acagcatcag cctgaacaac   2880

gagtacacca tcatcaactg catggagaac aacagcggct ggaaggtgag cctgaactac   2940

ggcgagatca tctggaccct gcaggacacc caggagatca agcagcgcgt ggtgttcaag   3000

tacagccaga tgatcaacat cagcgactac atcaaccgct ggatcttcgt gaccatcacc   3060

aacaaccgcc tgaacaacag caagatctac atcaacggcc gcctgatcga ccagaagccc   3120

atcagcaacc tgggcaacat ccacgccagc aacaacatca tgttcaagct ggacggctgc   3180

cgcgacaccc accgctacat ctggatcaag tacttcaacc tgttcgacaa ggagctgaac   3240

gagaaggaga tcaaggacct gtacgacaac cagagcaaca gcggcatcct gaaggacttc   3300

tggggcgact acctgcagta cgacaagccc tactacatgc tgaacctgta cgaccccaac   3360

aagtacgtgg acgtgaacaa cgtgggcatc cgcggctaca tgtacctgaa gggcccccgc   3420

ggcagcgtga tgaccaccaa catctacctg aacagcagcc tgtaccgcgg caccaagttc   3480

atcatcaaga agtacgccag cggcaacaag gacaacatcg tgcgcaacaa cgaccgcgtg   3540

tacatcaacg tggtggtgaa gaacaaggag taccgcctgg ccaccaacgc cagccaggcc   3600

ggcgtggaga agatcctgag cgccctggag atccccgacg tgggcaacct gagccaggtg   3660

gtggtgatga agagcaagaa cgaccagggc atcaccaaca agtgcaagat gaacctgcag   3720

gacaacaacg gcaacgacat cggcttcatc ggcttccacc agttcaacaa catcgccaag   3780

ctggtggcca gcaactggta caaccgccag atcgagcgca gcagccgcac cctgggctgc   3840

agctgggagt tcatccccgt ggacgacggc tggggcgagc gccccctg                3888
```

```
<210> SEQ ID NO 6
<211> LENGTH: 63
<212> TYPE: DNA
<213> ORGANISM: Artificial Sequence
<220> FEATURE:
<223> OTHER INFORMATION: Secretory signal from murine IgG (Kappa)

<400> SEQUENCE: 6

atggagaccg acaccctgct gctgtgggtg ctgctgctgt gggtgcccgg cagcaccggc     60

gac                                                                   63

<210> SEQ ID NO 7
<211> LENGTH: 6
<212> TYPE: PRT
<213> ORGANISM: Artificial Sequence
<220> FEATURE:
<223> OTHER INFORMATION: peptide

<400> SEQUENCE: 7

Leu Val Pro Arg Gly Ser
1               5

<210> SEQ ID NO 8
<211> LENGTH: 6
```

-continued

```
<212> TYPE: PRT
<213> ORGANISM: Artificial Sequence
<220> FEATURE:
<223> OTHER INFORMATION: peptide

<400> SEQUENCE: 8

Leu Val Pro Arg Gly Ser
1               5
```

UNITED STATES PATENT AND TRADEMARK OFFICE
CERTIFICATE OF CORRECTION

PATENT NO. : 11,707,510 B2
APPLICATION NO. : 16/970320
DATED : July 25, 2023
INVENTOR(S) : Jonas Funer It is certified that error appears in the above-identified patent and that said Letters Patent is hereby corrected as shown below:

In the Drawings

On Sheet 1 of 4, Lines 9-10 (Approx.), Figure 1, delete "20µg 20µl" and insert --20µg/20µl--.

On Sheet 1 of 4, Lines 13-14 (Approx.), Figure 1, delete "2µg 20µl" and insert --2µg/20µl--.

In the Specification

In Column 1, Line 66, delete "hemagglutins" and insert --hemagglutinins--.

In Column 4, Line 52, delete "hyperhydrosis." and insert --hyperhidrosis.--.

In Column 5, Line 10, delete "mouse." and insert --mouse--.

In Column 9, Line 31, delete "NIS" and insert --NTS--.

In Column 12, Line 45 (Approx.) delete "and or" and insert --and/or--.

In the Claims

In Column 43, Claim 3, Line 30 (Approx.), delete "hyperhydrosis." and insert --hyperhidrosis.--.

Signed and Sealed this
Nineteenth Day of March, 2024

*Katherine Kelly Vidal*

Katherine Kelly Vidal
*Director of the United States Patent and Trademark Office*